(12) United States Patent
Terui

(10) Patent No.: US 7,078,721 B2
(45) Date of Patent: Jul. 18, 2006

(54) OBJECT DETECTION APPARATUS FOR A VEHICLE

(75) Inventor: Takekazu Terui, Kariya (JP)

(73) Assignee: DENSO Corporation, Kariya (JP)

( * ) Notice: Subject to any disclaimer, the term of this patent is extended or adjusted under 35 U.S.C. 154(b) by 0 days.

(21) Appl. No.: 11/048,193

(22) Filed: Feb. 1, 2005

(65) Prior Publication Data

US 2005/0184259 A1    Aug. 25, 2005

(30) Foreign Application Priority Data

Feb. 19, 2004   (JP)   .............................. 2004-043179

(51) Int. Cl.
*G01N 21/88* (2006.01)
*G01N 21/86* (2006.01)
*G01V 8/00* (2006.01)

(52) U.S. Cl. ........................... 250/559.45; 250/559.42; 356/4.01; 356/237.2; 356/239.7; 340/903

(58) Field of Classification Search ........... 250/559.42, 250/559.45, 221, 222.1; 356/4.01, 237.2, 356/237.6, 239.7; 702/97, 158; 180/168–169; 340/903; 342/458; 701/96
See application file for complete search history.

(56) References Cited

U.S. PATENT DOCUMENTS

| 5,210,592 A | * | 5/1993 | Bretschneider ............. 356/613 |
| 5,675,518 A | | 10/1997 | Kuroda et al. |
| 5,920,382 A | * | 7/1999 | Shimizu et al. ............ 356/3.14 |

FOREIGN PATENT DOCUMENTS

| JP | 5-64999 | 8/1993 |
| JP | 2002-031685 | 1/2002 |

* cited by examiner

*Primary Examiner*—Stephone B. Allen
*Assistant Examiner*—Patrick J. Lee
(74) *Attorney, Agent, or Firm*—Harness, Dickey & Pierce, PLC

(57) ABSTRACT

An object detection apparatus for a vehicle includes a light emitter covered with an emission window, a light receptor covered with a reception window, a defect detection light emitter, a defect detection light receptor and a fracture detection circuit. The light emitter emits a light in front of the vehicle. The light receptor receives the light reflected by an object. The defect detection light emitter emits a detection light into one side of at least one of the emission and reception windows. The defect detection light receptor receives the detection light transmitted through the at least on emission and reception windows at another side. The fracture detection circuit determines whether either of the emission and reception windows are fractured based on the detection light received by the defect detection light receptors.

9 Claims, 3 Drawing Sheets

OBJECT DETECTION APPARATUS FOR A VEHICLE

CROSS REFERENCE TO RELATED APPLICATION

This application is based upon and claims the benefit of priority of Japanese Patent Application No. 2004-043179 filed on Feb. 19, 2004, the content of which is incorporated herein by reference.

FIELD OF THE INVENTION

The present invention relates to an object detection apparatus for a vehicle, which is especially suitable for detecting a distance to a forward vehicle using an electromagnetic wave.

BACKGROUND OF THE INVENTION

A conventional object detection apparatus intermittently emits a laser light and detects the laser light reflected by an obstacle such as a forward vehicle to detect a distance to the obstacle based on a time lag between the emission and the detection of the laser light.

JP2002-031685A discloses an object detection apparatus for a vehicle comprising a light emitter for emitting laser light, a pivotally-movable polygon mirror for reflecting the laser light to a scanning range in front of the vehicle, and a photoreceptor for detecting the laser light reflected by an obstacle.

The object detection apparatus, which is exposed to a harsh environment during vehicle travel, contains scanning mechanisms, optical devices, and electric circuits such as those described above in a housing to protect them from dirt, scattering stones, and water. Additionally, the housing has a light emission portion and a light reception portion that are made of a transparent material.

When the object detection apparatus is used for detecting the presence of and/or a distance to a forward obstacle, the apparatus is installed on a front face of the vehicle. Thus, the light emission and reception windows of the apparatus are often damaged by scattering stones and other loose debris commonly found on roadways.

If the object detection apparatus stops operating due to the damage, an electric control unit (ECU) turns off the apparatus and alarms a driver of the vehicle that the object detection apparatus is suffering a breakdown.

However, the object detection apparatus may continue to operate while the light emission and/or reception windows include fractures. In this case, the fractures may allow dirt and/or water to pass into the apparatus, thereby causing condensation or rust to accumulate on the devices in the apparatus. This impairs the operational performance of the apparatus such that it may cause an erroneous distance detection and/or a decrease in the detection range.

SUMMARY OF THE INVENTION

An object of the present invention is to provide an object detection apparatus for a vehicle, which can detect a fracture in either a light emission window or a light reception window thereof.

To achieve the above object, an object detection apparatus according to the present invention includes an electromagnetic emission portion, an electromagnetic reception portion, an emission window, a reception window, a defect detection light emission portion, a defect detection light reception portion, and a fracture detection portion.

The electromagnetic emission portion emits an electromagnetic wave in front of the vehicle. The electromagnetic reception portion receives the electromagnetic wave subsequent to it being reflected by an object located in front of the vehicle. The emission window covers the electromagnetic emission portion and enables the passage of the electromagnetic wave therethrough. The reception window covers the electromagnetic reception portion and enables the passage of the electromagnetic wave therethrough.

The defect detection light emission portion emits a detection light into one side of at least one of the emission window and the reception window. The defect detection light reception portion receives the detection light transmitted by the defect detection light emission portion at a second side of the at least one of the emission window and the reception window. The fracture detection portion determines whether the at least one of the emission window and the reception window is fractured based on the detection light received by the light reception portion.

BRIEF DESCRIPTION OF THE DRAWINGS

Other features and advantages of the present invention will be appreciated, as well as methods of operation and the function of the related parts, from a study of the following detailed description, the appended claims, and the drawings, all of which form a part of this application. In the drawings:

DETAILED DESCRIPTION OF THE PREFERRED EMBODIMENTS

Figure 1:
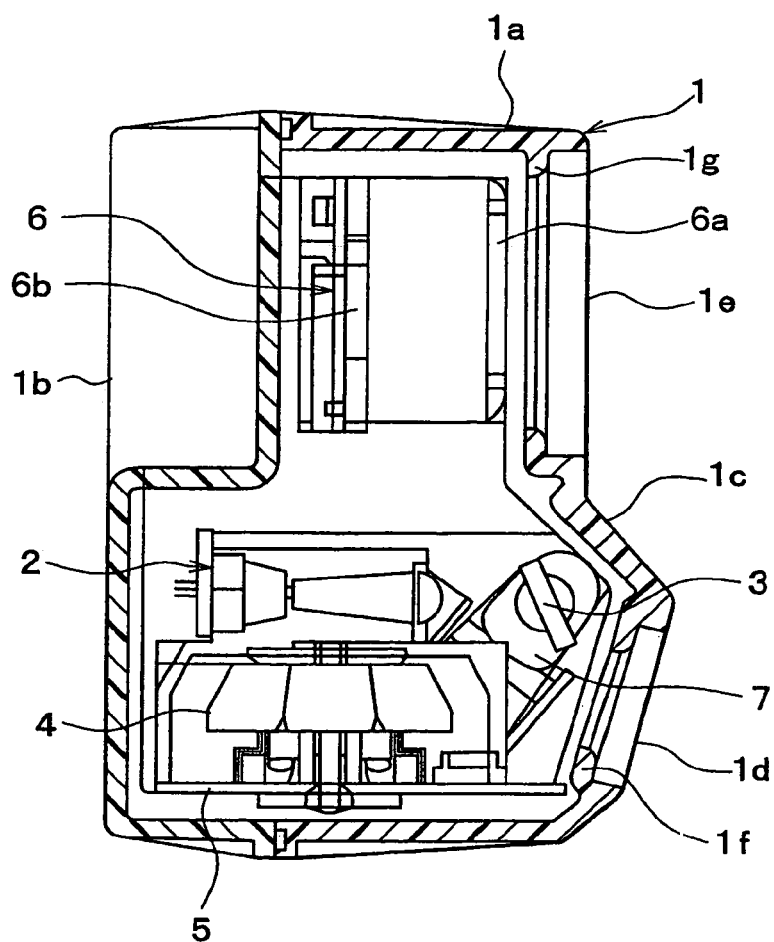
FIG. 1 is a cross-sectional view of an object detection apparatus of a first embodiment of the present invention taken through line I—I of FIG. 2.
Figure 2:
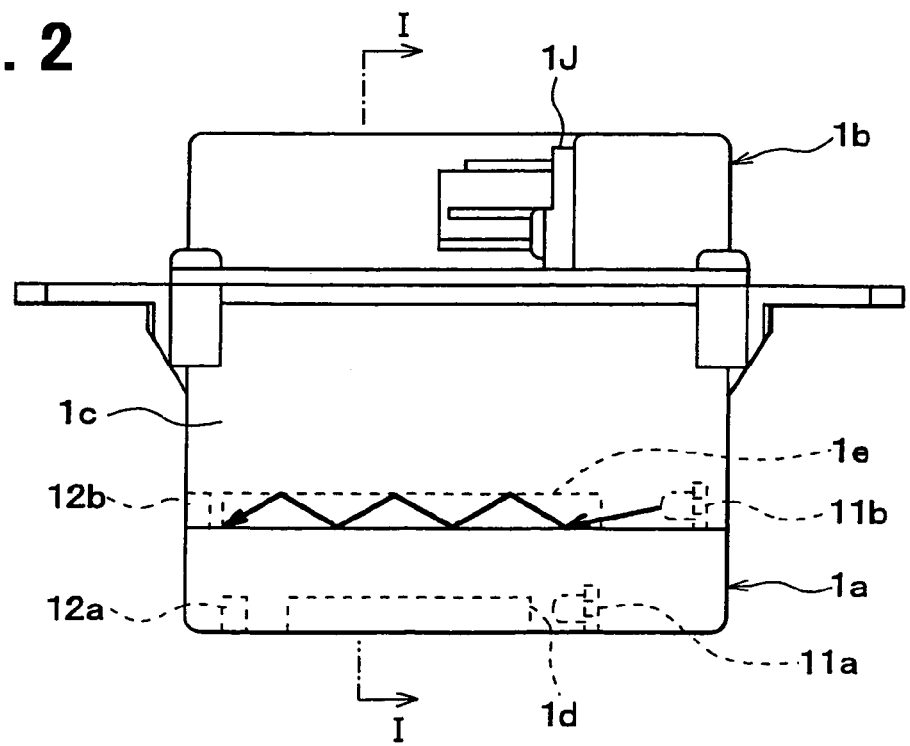
FIG. 2 is a partially hidden top view of the object detection apparatus of the first embodiment of the present invention.

FIG. 1 depicts a cross-sectional view of an object detection apparatus of the first embodiment. FIG. 2 depicts a partially hidden top view of the object detection apparatus. In FIG. 1, the right side coincides with a front side of the vehicle. The object detection apparatus is located on a vehicle and serves as a laser or radar device for measuring a distance between the vehicle and another vehicle in an adaptive cruise control system.

A housing 1 of the object detection apparatus is a plastic box. The housing 1 includes a first portion 1a and a second portion 1b. The first portion 1a is a container having an opening at a rear side thereof when installed on the vehicle and encloses components that will be described below.

The first portion 1a has a generally black-colored plastic portion 1c, a light emission window 1d, and a light reception window 1e. The light emission window 1d and the light reception window 1e are disposed at a front side of the housing 1 when installed on the vehicle. The light emission window 1d and the light reception window 1e are arranged generally vertically, although the light emission window 1d is slightly slanted, and they are made of a transparent material such as glass or acrylic.

Figure 3:
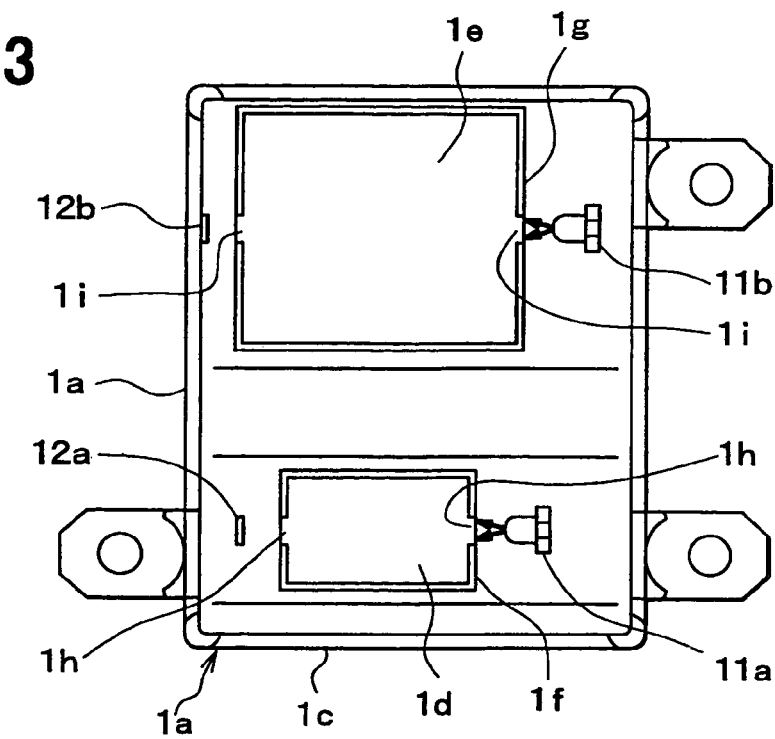
FIG. 3 is a rear view of the object detection apparatus of FIGS. 1 and 2 with a second portion removed therefrom.

FIG. 3 depicts a rear view of the object detection apparatus of the first embodiment of the present invention with the second portion 1b removed to expose the inside of the first portion 1a. The first portion 1a has two generally rectangular frames 1f and 1g disposed therein and containing the light emission window 1d and the light reception window 1e, respectively. Each of the frames 1f and 1g has a pair of opposing gaps receiving a pair of opposing projections 1h, 1i formed on the light emission window 1d and the light reception window 1e, respectively.

The frames 1f, 1g contain the light emission window 1d and the light reception window 1e, respectively, so as to expose side end faces of the projections 1h, 1i at opposite sides of the frames 1f, 1g. Imaginary lines (not shown) extending between the projections 1h, 1i pass through a generally central portion of the light emission window 1d and the light reception window 1e.

Referring back to FIG. 2, the second portion 1b of the housing 1 is made of plastic and holds a connector 1j partially protruding therefrom. The connector 1j is used to provide electrical communication between the object detection apparatus and a main electrical control unit (ECU) of the vehicle.

Referring now to FIG. 1, the housing 1 encloses a light emitter 2, a reflector 3, a polygonal mirror 4, and a circuit board 5 in a lower portion thereof. The circuit board 5 includes a control portion for controlling the object detection apparatus. The housing 1 further encloses a photoreceptor 6 in an upper portion thereof facing the light reception window 1e.

The light emitter 2 emits laser light to the reflector 3 according to driving signals sent by the control portion of the circuit board 5. In one embodiment, a laser diode generates a pulsed laser light and serves as the light emitter 2.

The reflector 3 reflects the laser light emitted by the light emitter 2 toward the polygonal mirror 4. A holder 7 pivotally supports the reflector 3. An actuator adjusts a vertical reflection angle of the reflector 3 according to driving signals sent by the control portion of the circuit board 5. In one embodiment, the reflector 3 has a pivot range of approximately ±1 degree.

The polygonal mirror 4 is a generally truncated hexagonal pyramid. The polygonal mirror 4 is supported above the circuit board 5 for rotational displacement around an axis of the pyramid. An actuator rotates the polygonal mirror 4 around the axis according to driving signals sent by the control portion of the circuit board 5. Thus, each side surface of the polygonal mirror 4 can serve as a reflection mirror.

Specifically, the polygonal mirror 4 reflects the laser light received from the reflector 3 forward in front of the vehicle through the light emission window 1d. The actuator changes a reflection angle of the laser light by changing the rotational orientation of the polygonal mirror 4 to adjust the emission angle of the laser light to scan over a predetermined range in front of the vehicle.

The circuit board 5 includes a plurality of devices composing the control portion such as a distance detection portion and a fracture detection portion. The distance detection portion calculates a distance between the vehicle and a forward vehicle. The fracture detection portion is operable to determine if either the light emission window 1d or the light reception window 1e is fractured. The control portion generates driving signals to operate the devices including the light emitter 2, the reflector 3, and the polygonal mirror 4. The control portion also receives signals from sensors such as the photoreceptor 6 and photoreceptors 12a, 12b. The control portion uses this information to calculate the distance to the forward vehicle and to detect the presence of a fracture in either the light emission window 1d or the light detection window 1e.

The photoreceptor 6 is located generally above the polygonal mirror 4 and is arranged in a substantially vertical plane. The photoreceptor 6 has a Fresnel lens 6a and a photoreception device 6b such as a photodiode. It should be appreciated that the photoreceptor 6 may also include additional or supplemental elements that may be required to achieve the principles of the present invention. The Fresnel lens 6a gathers the laser light entered through the light reception window 1e onto the photoreception device 6b. The photoreception device 6b generates an output current or an output voltage according to an intensity of the laser light gathered by the Fresnel lens 6a. The output current or the output voltage is sent to the control portion.

The housing 1 further encloses LEDs (light-emitting diodes) 11a, 11b (shown in FIGS. 2 and 3) and the photoreceptors 12a, 12b. The LEDs 11a, 11b serve as the defect detection light emission portion of the present invention. The photoreceptors 12a, 12b serve as the defect detection light reception portion of the present invention. The LEDs 11a, 11b and the photoreceptors 12a, 12b together with the fracture detection portion of the control portion of the circuit board 5 are used for detecting the presence of a fracture in either or both of the light emission and reception windows 1d, 1e. The LEDs 11a, 11b and the photoreceptors 12a, 12b are located close to the light emission and reception windows 1d, 1e, as shown in FIG. 3.

Specifically, LED 11a is located close to one projection 1h of the light emission window 1d and photoreceptor 12a is located close to the opposite projection 1h of the light emission window 1d. Furthermore, LED 11b is located close to one projection 1g of the light reception window 1e and photoreceptor 12b is located close to the opposite projection 1g of the light reception window 1e.

Thus, the light emitted by the LEDs 11a, 11b enters the light emission and reception windows 1d, 1e via the one projections 1h, 1g and is received by the photoreceptors 12a, 12b located at the opposite projections 1h, 1i.

How the object detection apparatus operates will now be described.

For an instance, while an adaptive cruise control system is operating, the distance detection portion of the control portion of the circuit board 5 operates to detect the distance between the vehicle and the forward vehicle.

First, the light emitter 2 emits laser light in front of the vehicle, via the reflector 3, the polygon mirror 4, and the light emission window 1d. When an obstacle such as a forward vehicle reflects the laser light, the reflected laser light enters through the light reception window 1e and is received by the photoreceptor 6b.

Thus, the photoreceptor 6b generates an output current or an output voltage according to the intensity of the laser light received. The control circuit detects the output current or the output voltage and calculates the distance D between the vehicle and the forward vehicle based on a time lag T between the emission and the reception of the laser light. An exemplary equation is:

$D = C \times T/2$, wherein $C$ is the velocity of the laser light.

Thus, the distance between the vehicle and the forward vehicle is detected. The distance is transmitted via the connector 1j to certain devices located outside the housing 1 such as an engine ECU and/or a braking ECU. Thus, the engine ECU and/or the braking ECU controls the engine power and the braking magnitude to keep the distance between the vehicle and the forward vehicle at a predetermined value.

Figure 4A:
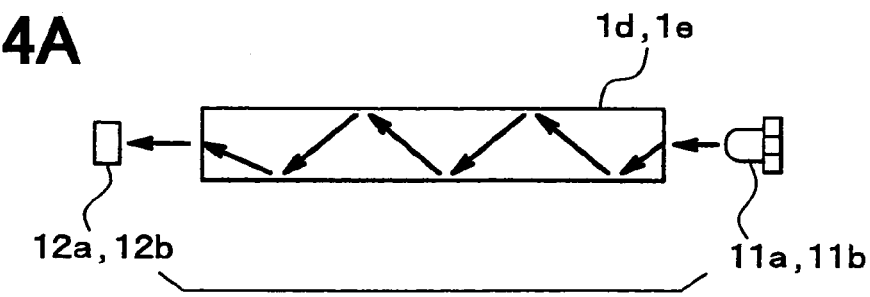
FIG. 4A is an end view of a window undergoing a fracture detection process in accordance with the object detection apparatus of FIG. 1.
Figure 4B:
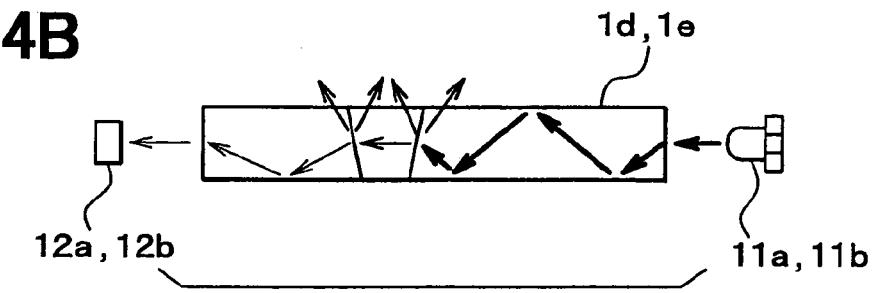
FIG. 4B is an end view of a fractured window undergoing a fracture detection process in accordance with the object detection apparatus of FIG. 1.

Furthermore, turning on the adaptive cruise control system also activates the fracture detection portion of the control portion to operate a fracture detection process. FIG. 4A depicts an optical path of the fracture detection process when the light emission or reception window 1d, 1e is not fractured. FIG. 4B depicts an optical path of the fracture detection process when the light emission or reception window 1d, 1e is fractured. The fracture detection process is now described. It should be appreciated that the fracture detection processes performed on the light emission window 1d and the light reception window 1e are identical and, therefore, a single process will be described referring to both windows 1d, 1e, as identified in FIG. 4.

When the light emission/reception window 1d, 1e is not fractured, as shown in FIG. 4A, the light emitted by the LED 11a, 11b enters the light emission/reception window 1d, 1e at the one projection 1h, 1i, as described above and shown in FIG. 3. The light emission/reception window 1d, 1e transmits the light to the opposite projection 1h, 1i. The light emission/reception window 1d, 1e has no light shielding or diffusing portion and, therefore, transmits generally 100% of the light entering through the one projection 1h, 1i to the opposite projection 1h, 1i. The photoreceptor 12a, 12b receives the light reaching the other projection 1h, 1i and outputs an output current or an output voltage having a value based on an intensity of the light. The output current or the output voltage generated by the photoreceptor 12a, 12b is then sent as a fracture detection signal to the control portion of the circuit board 5.

When the light emission/reception window 1d, 1e is fractured, as shown in FIG. 4B, the light emitted by LED 11a, 11b enters the light emission/reception window 1d, 1e at the one projection 1h, 1i in the same manner as described above. However, the fractures in the light emission/reception window 1d, 1e cut off or diffuse the light. Thus, the fractures cause the intensity of the light received by the opposite projection 1h, 1i to be reduced to generally 50% of that when the light emission/reception window 1d, 1e was not fractured. The photoreceptor 12a, 12b then generates an output current or an output voltage based on the intensity of the light received. The detection current or the detection voltage outputted by the photoreceptor 12a, 12b is inputted as a fracture detection signal to the control portion located on the circuit board 5.

Figure 5:
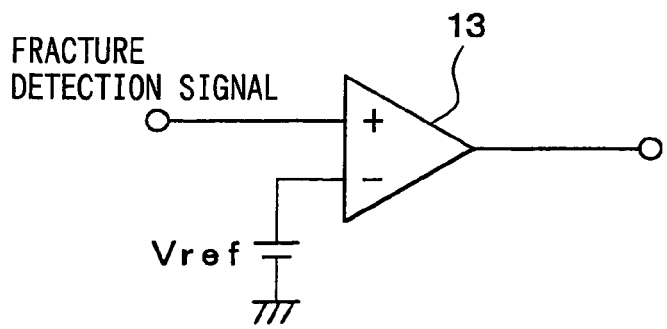
FIG. 5 is a schematic diagram of a fracture detection portion of the object detection apparatus of FIG. 1.

The fracture detection portion of the control portion of the circuit board 5 determines whether the light emission/reception window 1d, 1e is fractured based on the fracture detection signal sent from the photoreceptor 12a, 12b. The fracture detection portion of the circuit board also includes a comparator 13, shown in FIG. 5. The comparator 13 realizes the fracture detection portion. The fracture detection portion compares the voltage output by the photoreceptor 12a, 12b with a reference voltage or transforms the output current to an output voltage to compare with the reference voltage. The fracture detection portion determines that the light emission/reception window 1d, 1e is not fractured when the output voltage is larger than the reference voltage and determines that the light emission/reception window 1d, 1e is fractured when the detection voltage is smaller than the reference voltage.

It should be appreciated that the reference voltage may be set equal to a value of the output voltage generated when the light emission/reception window 1d, 1e has only one fracture. Alternatively, the reference voltage may be set equal to a value of the output voltage generated when the light emission/reception window 1d, 1e multiple fractures, thereby reducing object detection performance.

The fracture detection process can detect fractures in the light emission/reception window 1d, 1e as described above. When the control portion detects the presence of a fracture in either the light emission window 1d or the light reception window 1e, the control portion outputs a signal to the vehicle ECU indicating such via the connector 1j. The signal activates an alarm lamp (not shown) located on an instrument panel of the vehicle and/or an information lamp located on a meter panel to notify a driver whether the cruise control operation is executable.

As described above, the object detection apparatus according to the first embodiment determines whether either the light emission window 1d or the light reception window 1e is fractured. This is accomplished by emitting a light into one side of the light emission or reception window 1d, 1e and receiving the light at an opposite side thereof. By fixing or replacing the fractured light emission/reception window 1d, 1e, it is possible to prevent the object detection apparatus from suffering further damage from events such as the entry of dirt or water and/or the accumulation of rust, which all may impair the performance of the apparatus.

Figure 6:
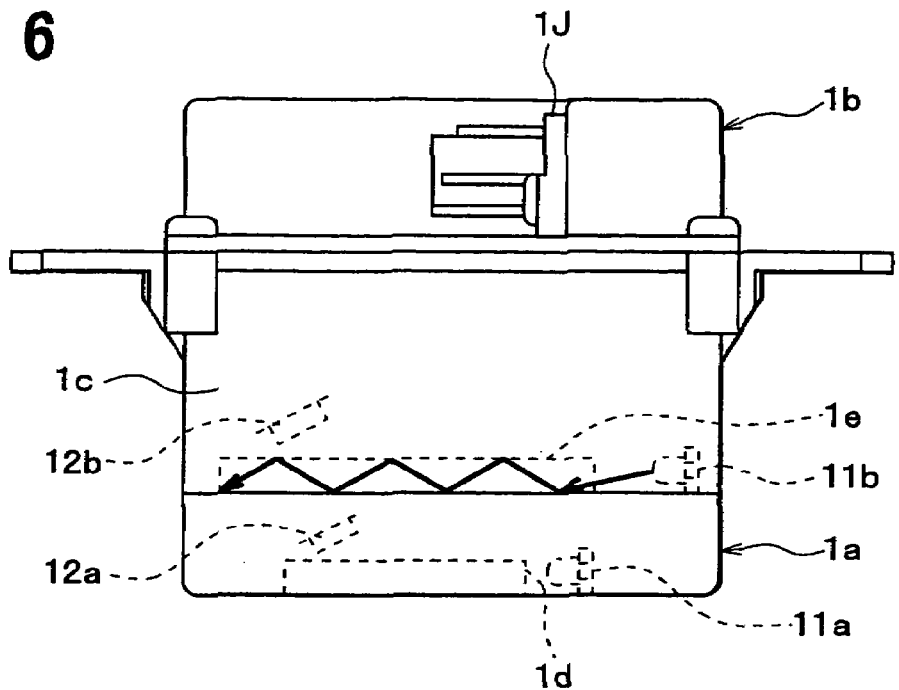
FIG. 6 is a partially hidden top view of a second embodiment of an object detection apparatus according to the principles of the present invention.
Figure 7A:
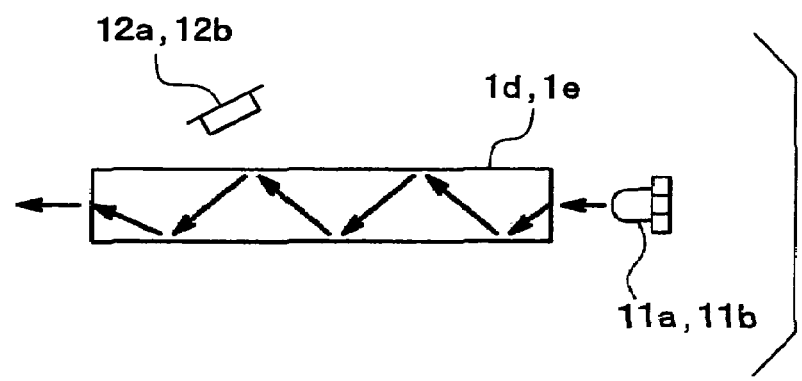
FIG. 7A is an end view of a window undergoing a fracture detection process in accordance with the object detection apparatus of FIG. 6.
Figure 7B:
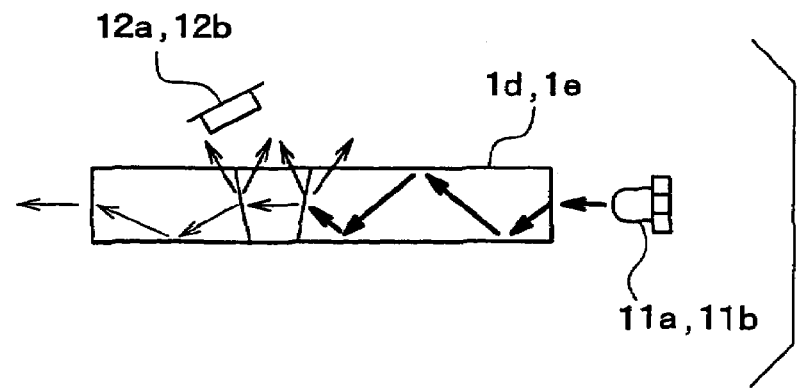
FIG. 7B is an end view of a fractured window undergoing a fracture detection process in accordance with the object detection apparatus of FIG. 6.

FIG. 6 depicts a partially hidden top view of a second embodiment of an object detection apparatus according to the present invention. FIG. 7A depicts an optical path generated through a light emission window 1d or a light reception window 1e that is not fractured. FIG. 7B depicts an optical path generated through a light emission window 1d or a light reception window 1e that is fractured. The object detection apparatus according to this embodiment has generally the same configuration as the first embodiment except for the locations of the photoreceptors 12a, 12b. The following description focuses on the portions of the second embodiment that are different from the first embodiment.

As shown in FIG. 6, the photoreceptors 12a, 12b are positioned to receive light emitted from a rear surface of the light emission or reception windows 1d, 1e. More specifically, each of the photoreceptors 12a, 12b face generally center portions of the light emission and reception windows 1d, 1e, respectively. This is where fractures tend to occur rather than in other portions of the light emission and reception windows 1d, 1e. Therefore, this arrangement of the photoreceptors 12a, 12b is for detecting the fractures generated in the center portion of the light emission and reception windows 1d, 1e.

When the light emission/reception window 1d, 1e is not fractured, as shown in FIG. 7A, the light emitted by the LED 11a, 11b transmits directly therethrough. Thus, the photoreceptor 12a, 12b does not receive any light. The photoreceptor 12a, 12b then generates an output current or an output voltage having a value corresponding to the intensity of the light received, which is small or near zero. The output current/voltage is inputted as the detection signal to the control portion of the circuit board 5.

When the light emission/reception window 1d, 1e is fractured, as shown in FIG. 7B, the fracture diffuses the light emitted by the LED 11a, 11b forcing the light out of the rear surface of the light emission /reception window 1d, 1e. Thus, the photoreceptor 12a, 12b receives the light diffused by the fractures. The photoreceptor 12a, 12b then generates an output current or an output voltage based on the intensity of the light received. The output current/voltage is inputted as the detection signal to the control portion located on the circuit board 5.

The fracture detection portion of the control portion determines whether the light emission/reception window 1d, 1e is fractured based on the detection signals sent from the photoreceptor 12a, 12b.

As described above, the object detection apparatus according to the second embodiment of the present invention detects the presence of a fracture in the light emission or reception window 1d, 1e based not on the intensity of the light passed through the entire width of the light emission/reception window 1d, 1e, but on the light diffused out of the rear surface of the light emission/reception window 1d, 1e. The object detection apparatus according to the second embodiment therefore has the same advantage as that of the first embodiment.

The object detection apparatuses according to the first and the second embodiments have LEDs 11a, 11b. In alternative embodiments, the LEDs 11a, 11b can be substituted with other light sources such as lasers or any other lamp operable to serve the principles of the present invention.

Furthermore, the photoreceptors 12a, 12b in an alternative embodiment of the object detection apparatus may be located at positions different from those in the first and second embodiments. For example, they may be located at upper and lower end faces of the light emission and reception windows 1d, 1e.

Additionally, the components of the object detection apparatus according to the first and the second embodiments may be arranged in different ways. For example, the light emission window 1d and the light reception window 1e have been described as being positioned generally vertically. However, the present invention is also applicable to an object detection apparatus having the light emission window and the light reception window positioned generally horizontally.

The object detection apparatuses according to the first and the second embodiments use a lightwave for object detection. However, the present invention is also applicable to an object detection apparatus using other electromagnetic detection waves such as millimeter waves. That is, the present invention is applicable to any object detection apparatus that detects a distance to and/or a presence of an object by emitting an electromagnetic wave with an emitter and receiving the electromagnetic wave reflected by the object with a receptor.

What is claimed is:

1. An object detection apparatus for a vehicle comprising:
   an electromagnetic emission portion for emitting an electromagnetic wave in front of the vehicle;
   an electromagnetic reception portion for receiving the electromagnetic wave reflected by an object;
   an emission window covering the electromagnetic emission portion and enabling the passage of the electromagnetic wave;
   a reception window covering the electromagnetic reception portion and enabling the passage of the electromagnetic wave;
   a defect detection light emission portion for emitting a detection light to a first surface of at least one of the emission window and the reception window;
   a defect detection light reception portion for receiving the detection light from a second surface of the at least one of the emission window and the reception window; and
   a fracture detection portion for determining whether either of the at least one of the emission window and the reception window have a fracture based on the detection light received by the defect detection light reception portion.

2. The object detection apparatus of claim 1, wherein the first surface is substantially parallel and opposite to the second surface.

3. The object detection apparatus of claim 2, wherein the first surface and second surface are end side surfaces of the at least one of the emission window and the reception window.

4. The object detection apparatus of claim 1, wherein defect detection light emission portion and the defect detection light reception portion are substantially axially aligned.

5. The object detection apparatus of claim 1, wherein the first surface is substantially perpendicular to the second surface.

6. The object detection apparatus of claim 5, wherein the first surface is an end side surface and the second surface is a rear face of the at least one of the emission window and the reception window.

7. An object detection apparatus for a vehicle comprising:
   an electromagnetic emission portion for emitting an electromagnetic wave in front of the vehicle;
   an electromagnetic reception portion for receiving the electromagnetic wave reflected by an object;
   an emission window covering the electromagnetic emission portion and enabling the passage of the electromagnetic wave;
   a reception window covering the electromagnetic reception portion and enabling the passage of the electromagnetic wave;
   a defect detection light emission portion for emitting a detection light into an end surface of at least one of the emission window and the reception window;
   a defect detection light reception portion for receiving the detection light transmitted by the defect detection light emission portion from a rear surface of the at least one of the emission window and the reception window; and
   a fracture detection portion for determining whether the at least one of the emission window and the reception window is fractured based on the detection light received by the defect detection light reception portion.

8. The object detection apparatus according to claim 7, wherein the defect detection light reception portion is configured to receive the detection light from a middle portion of the side surface of the at least one of the emission window and the reception window.

9. The object detection apparatus according to claim 7, wherein the end surface is substantially perpendicular to the rear surface.

* * * * *